United States Patent [19]

Sisti et al.

[11] 4,405,344
[45] Sep. 20, 1983

[54] METHOD AND EQUIPMENT FOR VOLUMETRICALLY CONTROLLED AND REPRODUCIBLE INTRODUCTION OF SMALL AMOUNTS OF LIQUID SAMPLES INTO CHROMATOGRAPHIC ANALYSIS SYSTEMS

[75] Inventors: Giorgio Sisti, Milan, Italy; Sorin Trestianu, Brussels, Belgium; Ermete Riva, Como, Italy

[73] Assignee: Carlo Erba Strumentazione S.p.A., Rodano, Italy

[21] Appl. No.: 304,780

[22] Filed: Sep. 23, 1981

[30] Foreign Application Priority Data

Sep. 30, 1980 [IT] Italy ............................ 25018 A/80
May 4, 1981 [IT] Italy ............................ 21504 A/81

[51] Int. Cl.³ ............................................. B01D 15/08
[52] U.S. Cl. ..................................... 55/67; 55/197; 55/386
[58] Field of Search ..................... 55/197, 67, 386

[56] References Cited

U.S. PATENT DOCUMENTS 3,366,149 1/1968 Taft et al. ...................... 55/197 X
4,035,168 7/1977 Jennings ........................ 55/197 X

*Primary Examiner*—John Adee
*Attorney, Agent, or Firm*—Millen & White

[57] ABSTRACT

A method and apparatus for controllably and reproducibly introducing small amounts of a liquid sample into chromatographic systems, especially high resolution gas chromatographic systems and thin-layer chromatographic systems, order to obtain sampling extremely reduced in volume and presenting maximum reliability and reproducibility, uses a sample container having a pipette-like or nozzle-like outlet neck of very small diameter. The liquid placed in the container is submitted to at least one pressure pulse which is controlled in time and/or amplitude in order to determine emission of a corresponding and controlled quantity of liquid from the outlet neck. The pressure pulse can be a pneumatic pulse directly applied to the liquid sample in the container, or a mechanical pulse applied to the liquid sample through a device acting by magnetostriction or by a piezoelectric system.

22 Claims, 9 Drawing Figures

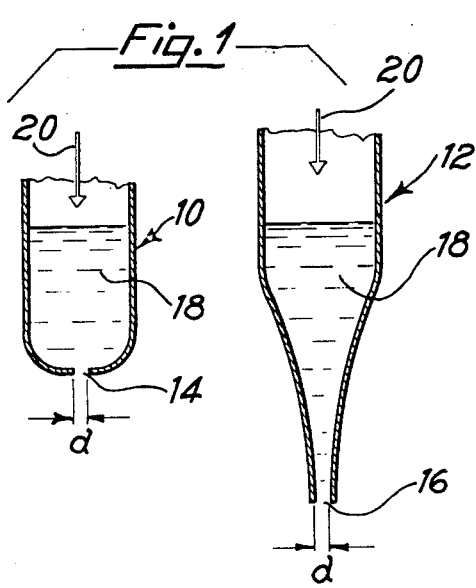
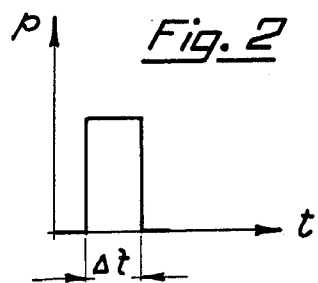
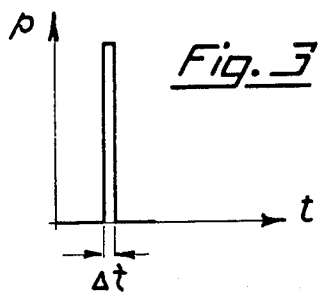
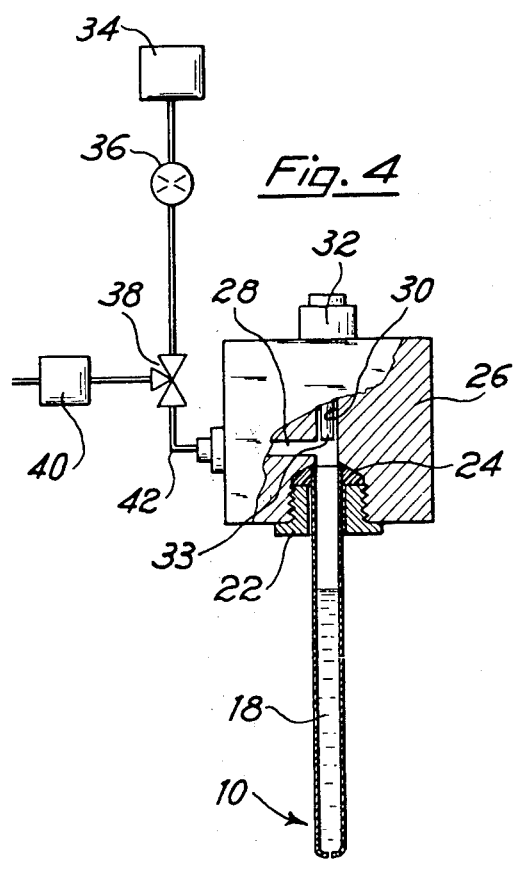
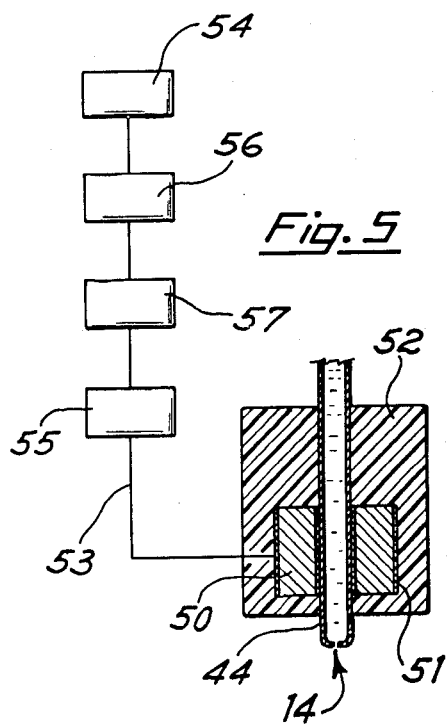

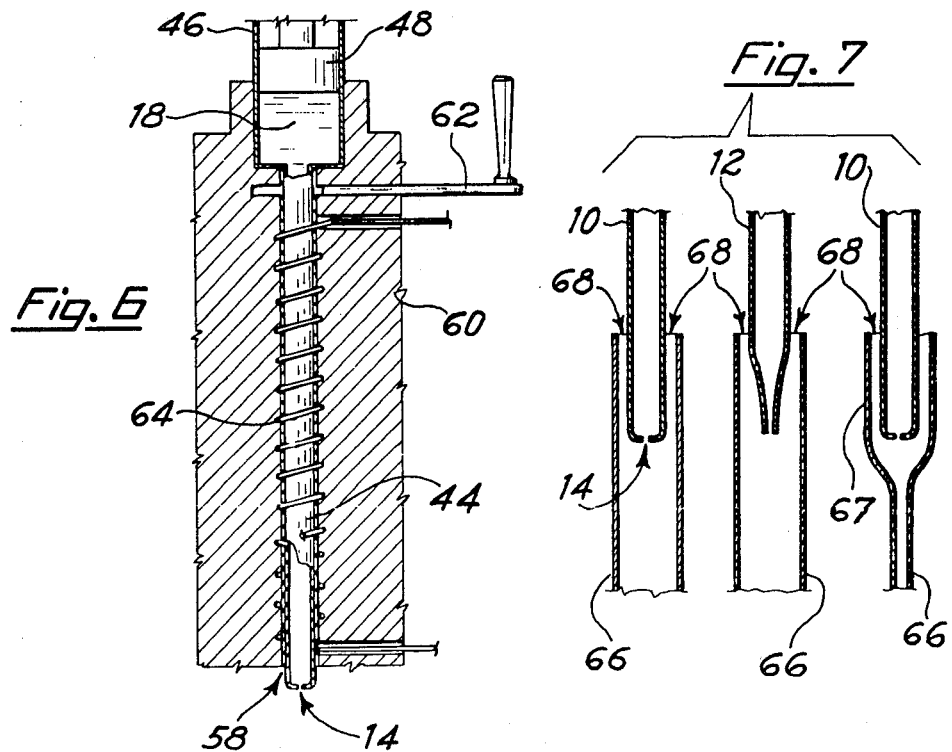
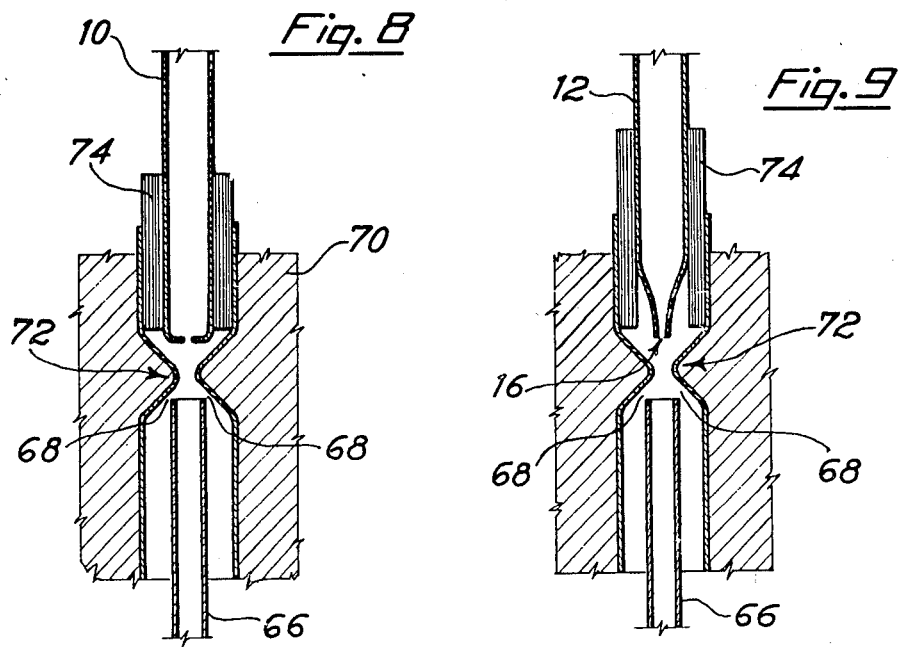

METHOD AND EQUIPMENT FOR VOLUMETRICALLY CONTROLLED AND REPRODUCIBLE INTRODUCTION OF SMALL AMOUNTS OF LIQUID SAMPLES INTO CHROMATOGRAPHIC ANALYSIS SYSTEMS

BACKGROUND OF THE INVENTION

1. Field of the Invention

The present invention relates to a method and an apparatus to perform sampling in chromatographic systems with very small amounts of liquid sample, said method and said equipment being particularly but not exclusively applicable to high resolution gas chromatographic systems, with capillary or micropacked columns, or to thin-layer chromatographic systems. Use of this method and apparatus makes it possible to perform controllable and reproducible sampling of very small amounts of sample, with values unattainable through the techniques usually employed for liquid sampling in chromatographic systems and particularly using microsyringes or pipettes.

2. Description of the Prior Art

The microsyringes used in chromatography are generally of the type with calibrated body (capable of sampling amounts ranging from 0.2 to 10 microliters) or of the type with calibrated needle, where the piston penetrates into the needle. The latter microsyringes are capable of handling smaller quantities of samples, in a reliable and reproducible way, but only within certain limits, in particular with lower limits of about 200-300 nanoliters. Below this limit, the high surface tension of the liquid and the relatively reduced speed of the piston movement do not allow the drop, which has formed at the needle end, to fall from it, considering the reduced diameter of the outlet nozzle of the needle. Precision is moreover negatively affected by poor sealing between piston and calibrated needle.

Another known system is the sampling system commonly used in the laboratory and named "pipette system", in which a calibrated tubing is filled with a liquid to be transferred, by sucking it into the tubing, the liquid amount placed in the tubing is controlled and the same is retained in the tubing by closing same at the end where aspiration has been carried out. Then, an injection of the liquid into a receiving container is made by opening said end. This sampling method or transfer method of determined amounts of liquid is well known and has been used in gas chromatography too, but however only for quantities usually measurable in a rather rough way, even if the literature reports a lower limit of 25–50 nanoliters (see R. Kaiser-Gas Phase Chromatography—Vol. 1 pp. 90-95—Butterworths 1963—London).

Therefore it can be considered that, of course according to the nature of the liquid substance to be sampled, a lower limit exists, generally between 50 and 200 nanoliters, below which it is not possible to go in reliable and reproducible sampling using microsyringes or micropipettes.

Furthermore, in the case of the pipettes, and also often in the case of the microsyringes, when the gaseous fluid between the piston and the sample liquid is not completely eliminated, considering that a quantitative determination is performed during feeding, it may occur that the gas pushing the liquid out of the pipette, enters the capillary column, which sometimes involves problems connected with the choice and the use of said gas, such that it does not affect analyses.

The above mentioned quantitative limitations, however, are such that the operator is often forced to perform accessory operations imposed by the relatively high quantities of sample that has to be introduced into the chromatographic system and particularly into the capillary column. In fact, especially in the case of direct injection without vaporization (oncolumn), particularly considered herein, the sample must be diluted in a dilution ratio which is often very high (of the order of 1:10000 or more), with an operation which may involve difficulties in the exact analytical determination of the sample and in that it can introduce discriminations or variations in the sample original conditions.

In other cases, a co-called "splitting" operation is necessary, that means the elimination of a high percentage of the quantity fed to the injector, before its introduction into the column, which operation may involve even higher risks of discriminations.

OBJECTS OF THE INVENTION

Accordingly, an object of the invention is to provide a method and apparatus making it possible to perform sampling in chromatographic systems with very small amounts of liquid sample; for instance from 10 picoliters to 50 nanoliters, in a reproducible way under the same sampling conditions and sample type.

Another object of the present invention is to provide a method and apparatus in which the introduction of said small or very small amounts of liquid sample does not require the parallel introduction into the chromatographic system of another substance, either a liquid or gaseous one to propel the sample out of the sampling container.

Still another object of the present invention is to provide a method and apparatus wherein the volumetric dosage of the substance injected into the chromatographic system is performed with the maximum of reliability, precision and reproducibility, during the injection stage itself.

SUMMARY OF THE INVENTION

According to the invention a method is provided for injecting very small quantities of liquid sample in chromatographic systems, especially in high resolution gas chromatographic systems or thin layer chromatographic systems, said method comprising the following steps:

preparing a sample container having a volume larger than the quantity to be sampled and having a pipette- or nozzle-shaped neck, acting as outlet, with a maximum size ranging between 1 and 100 $\mu$m, preferably between 1 and 30 $\mu$m;

filling said container with a sample quantity greater than the amount to be sampled and controlling that, in correspondence with said outlet, a meniscus of the sample liquid be formed;

introducing said container, or part of same, into an injector or a device for sample injection into the chromatographic system;

submitting the liquid inside the container to at least one pressure pulse having a pressure value sufficient to overcome the surface tension of the liquid sample in correspondence with the outlet and a duration limited in time according to said pressure value and to the quantity to be sampled, keeping into consideration the outlet size, the pressure pulse amplitude and the sample characteristics;

abruptly reducing the pulse pressure down to a value lower than the one sufficient to overcome the surface tension of the liquid in correspondence with the container outlet.

Therefore, according to said method, it is now possible to carry out sampling of extremely reduced quantities of liquid, using a container which can be of the substantially traditional type, except for the outlet neck, to which a device can be applied which allows to create said pressure pulse, in such a way that the sample drawing and eventual washing of the container can be performed with extremely simple and traditional systems and means, though being possible to perform said samplings with extremely reduced quantities.

Considering the performance of the system according to the invention, in most cases, the sample can be injected directly into the column, without vaporization. Vaporization may become necessary only in case of so-called "dirty" samples to prevent substances with high molecular weight contained in said samples from being directly introduced into the capillary column.

Said method according to the invention can be substantially performed according to two different ways, the first of which considers the application of a pneumatic pulse, obtained by operating for time periods of the order of milliseconds an electrovalve which makes it possible to exert a pressure in correspondence with a gaseous element directly or indirectly placed in contact with the sample in the container, while the second one considers the application, to the container body and/or to means mechanically connected with the same, of a mechanical pulse, obtained with a piezoelectric system, a magnetostrictive system or other similar system, which determines an extremely high and extremely quick pressure increase in the liquid.

As previously said, the invention relates also to an apparatus which, according to said method, makes it possible to perform samplings in chromatographic systems with small or very small quantities of liquid sample, in a reliable and reproducible way under the same operating conditions.

BRIEF DESCRIPTION OF THE DRAWINGS

FIG. 1 is an enlarged view, in axial section, showing possible shapes of the outlets of containers for samples to be used according to the invention.

FIGS. 2 and 3 are examples of possible pressure pulses used in the method and equipment according to the invention to perform desired sampling.

FIG. 4 is a diagrammatic view, with parts in section, of an apparatus for performing sampling by the use of pneumatic pulses.

FIGS. 5 and 6 diagrammatically show embodiments of apparatus for sampling by means of pressure pulses obtained with a piezoelectric system and magnetoscrictive system, respectively.

FIG. 7 is a diagrammatic view showing possible reciprocal positions of container outlets, in one of the types of apparatus previously illustrated, and the end of a capillary column in applications to high resolution gas chromatography with capillary columns.

FIGS. 8 and 9 are diagrammatic views of other possible positions of the sample container and of the end of the capillary column for the same uses as considered in FIG. 7.

DESCRIPTION OF THE PREFERRED EMBODIMENTS

The invention relates, as already said, to a method and an apparatus for sampling, in chromatographic systems, of liquid samples, said method and said apparatus being particularly applicable to laboratory chromatographic systems, especially in high resolution gas chromatography with capillary columns and with direct on-column injection of the sample, without previous vaporization, or to thin-layer chromatographic systems. In particular, chromatographic systems of the direct injection type are well known and applied, wherein the liquid sample is injected directly into the initial part of the column and then is moved along the latter by means of a carrier gas, the sample being simultaneously vaporized. The method and equipment according to the invention are capable, especially in chromatographic systems of the above mentioned type, of allowing injection of a quantity of liquid sample so reduced in volume that the entire quantity can be analyzed in the chromatographyc sistem, without any need of dilution, as is necessary in traditional methods and apparatus to obtain a precise dosage of the injected sample. Although larger amounts can also be injected, the method and apparatus which will be illustrated are particularly suitable for the injection in a reliable and reproducible way, of liquid samples in quantities ranging between 10 picoliters and 50 nanoliters, i.e., amounts so small that they could not be handled with the previously employed systems.

The method and the apparatus of the invention are based on the use of a container for the liquid sample which has a volume greater than that of the sample to be analyzed, said container being made of any suitable material, for instance glass, metal, fused silica or any other material, and having a pipette shape, a syringe needle shape or any other suitable shape.

The essential condition is that said container, as indicated by 10 or 12 in FIG. 1, presents a neck defining an outlet having a maximum size (a diameter d in this specific case) ranging from 1 to 100 μm, preferably between 1 and 30 μm. Said neck can be nozzle-shaped, as indicated by 14 in FIG. 1, and therefore has a preferred neck diameter d from 10 to 30 μm, or micropipette-shaped, as indicated by 16 in the same FIG. 1, with a preferred diameter d from 1 to 20 μm. The container, 10 or 12 as illustrated in FIG. 1, can be filled by the usual methods, for instance by means of a syringe, by gravity, by capillarity or in any way whatsoever, with a quantity of liquid 18 which is greater than the volume that is required to flow from the neck 14 or 16 to be analyzed in the chromatographic system. Once the container 10 or 12 has been fed with the sample 18, it is necessary to check, especially in the case of the container 12 with a pipette-like end, that the liquid goes as far as to reach the neck 14 or 16, forming a meniscus therein. Under these conditions, taking into account the reduced size of the neck, the surface tension of the liquid prevents the latter from flowing out of the neck, forming drops, this obviously provided that the neck 14 or 16 does not touch foreign bodies, as for instance the wall of the gas chromatographic column, which may help the liquid to flow outside the column. Once the feeding of the container 10 or 12 as previously indicated has been carried out, pressure on the liquid 18 is exerted directly or indirectly as schematically shown by the arrows 20 in FIG. 1 to eject a measured amount of liquid 18 through the neck 14 or 16. Said pressure is controlled in amplitude and in time as indicated in FIGS. 2 and 3, keeping into consideration that the liquid amount ejected depends both on the amplitude, namely the value of the pulse pressure, on the duration of the pulse itself and on the number of pulses.

As it can be seen from FIGS. 2 and 3, the pulse has a step configuration and it is very important that the downwards section of same, namely pressure return to zero, be placed vertically as much as possible in order to avoid during this stage, in correspondence to the neck 14 or 16, the formation of a drop which will remain in position, thus completely altering any measuring of the injected sample. In the case of FIG. 2, the pressure pulse is a pneumatic pulse and reaches a value $p_1$ which must be in any case higher than that necessary to overcome the surface tension of the liquid in correspondence with the neck 14 or 16. In relation to the pressure value $p_1$, the duration $\Delta t$ of the pulse is chosen, variable from about a millisecond to about a second, in order to obtain the desired quantities of ejected liquid.

The pressure values can range from 1 to 10 atmospheres. Alternatively, it can obsiously be possible to emit several pulses having lower duration. However, for an exact reproducibility of sampling, it is very important to reduce to the minimum the dead space, that is the gas volume on which each pressure pulse acts.

The situation illustrated in FIG. 3 is the one that occurs in case of a pressure pulse exerted by means of magnetostriction, or piezoelectricity. In this case, the time $\Delta t$ is extremely reduced and corresponds to the resonance frequency of the laminations forming the magnetostriction device or to the frequency of the piezoelectric material, ranging from 10 to 100 KHZ, while a certain regulation of the quantity emitted at each pulse can be performed by varying the amplitude of the electric pulse given to the device and consequently the pulse pressure value given to the liquid, said pressure value being in any case of one or several orders higher than that necessary in the pneumatic case.

An apparatus for carrying out the method according to the invention with pneumatic pulse is diagrammatically illustrated in FIG. 4, wherein a receiver 10 of the type illustrated in the left side of FIG. 1 is provided, which has preferably a very small inner diameter and which can be removably fixed, for example by means of a locking nut 22 and a gasket 24 compressed by said nut, in a supporting block 26 which presents a groove 28 for feeding gas under pressure, for instance air. The block 26 can present another groove 30 which can be closed by a locking element 32 to feed the container 10 with the sample 18. The locking element comprises a protrusion 33, for example in metal, to reduce to the minimum the dead space.

The duct 28 is connected, in any known way, to a circuit for supply of air under pressure coming from a source 34, said circuit comprising a pressure regulator 36 and an electrovalve 38, the opening time of which can be regulated by means of a device 40, known in itself. A duct 42 is positioned between the electrovalve 38 and block 26 and advantageously presents a very small inner size, in such a way to reduce to the minimum the so-called dead volume, that is the volume of air comprised between the valve 38 and the upper meniscus of liquid 18 within the container 10. Said reduction of the dead volume is very important to obtain a quick fall of pressure at the end of the pulse and then to be sure that no drop forms and adheres to the container 10 outlet.

The apparatus of FIG. 4 can be fed through the opening 32 for instance by means of a conventional syringe, with a sample quantity much greater than the one which must be used for injection into the gas chromatographic system. Once the feeding is performed, the opening 32 is closed, the container is introduced into the chromatographic system and the valve 38 is opened for a time period controlled by the device 40, in such a way as to create a pressure pulse having a value regulated by the element 36. In this way, a small jet of liquid forms and breaks out in small drops at a point which is farther from the outlet neck 14 the higher is the pressure value set in regulator 36, of course with the same type of liquid and same size of neck.

The sampling device illustrated in FIG. 5 operates with a piezoelectric system which, in its that part including the element for formation and emission of the jet of drops, is substantially configured like an ink-drops printing device, of the "jet on demand" type, known in itself. It essentially comprises a container 44, for example but not necessarily with a cylindric shape, made of glass or fused silica, ready to be filled in its lower section with the sample to be injected into the column for instance introduced through the upper section thereof.

The container 44 ends in its lower section with a calibrated nozzle 14, as previously indicated, through which the liquid jet of sample is emitted. Under atmospheric pressure conditions, the liquid does not flow out of the nozzle 14 because of its surface tension.

The container 44 is connected to a transducer 50 of a piezoelectric type, capable of provoking, when excited, a sudden volume variation inside the container 44 and therefore a sudden pressure variation in the liquid present in it, such as to determine the flowing out of a calibrated jet of one or more drops through the nozzle 14. The transducer 50, which is placed very near to the nozzle 14 and housed for example in a small block 52 made of plastic material, is excited by means of a source of electrical pulses 54, which have the characteristics previously described, feeding of the transducer 50 on its electrodes 51, through a circuit 53 having a switch 55 by means of which the operator can close the circuit and then control the emission of the jet of drops. To the source 54 a known means 56 is connected to vary the amplitude of pulse or pulses communicated to the transducer 50; another component 57 is also connected, capable of controlling the duration of the pulse or series of pulses.

For operation, the container 44 must be filled with the liquid sample, possibly by means of a microsyringe, at least in its section close to the nozzle 14, and the transducer 50 is submitted to a pulse or series of pulses having a predetermined amplitude, during which, in correspondence with the nozzle 14, a jet of one or more drops of sample liquid is emitted, in a small pre-settable quantity. Said jet presents high directionality and an extremely limited increase in diameter, so that it can be directed into a column with one of the systems which will be considered, for example through the injection port of a direct injector, equipped with a "slice" type or rotative valve.

The amplitude of pulses may be regulated by the element 56, in order to obtain a corresponding regulation of the pressure increase provoked by said pulses and consequently of a first parameter affecting the operative conditions, in particular of the correct formation of the jet of drops, considering the nozzle diameter and the nature of the treated liquid. When the other conditions are kept unchanged, the ejected quantity of a given sample, thanks to the formation of a pulse having a preset amplitude, is exactly definite and equal to a drop, and therefore the ejected quantity obtained by a series of pulses will depend only on the duration of the latter and therefore on the number of pulses forming such series, because the time period of each pulse is determined by the transducer characteristics.

The apparatus illustrated in FIG. 6 consists of a container 44 having a needle-syringe shape 46 with piston 48. The needle 44 is introduced into a duct 58 inside the body of an injector 60, of a type known in itself and provided with a valve 62, said injector body being provided with a magnetostriction apparatus 64, acting on the needle 44, which is made of nickel. The exerted pressure is sufficient for determining a sample ejection, in the desired quantity, independently from the position of the syringe piston 48, obviously provided that the liquid 18 fills the container 44 at least partly and as far as the outlet neck 14. Both in the case of a pneumatic-type pulse and in the case of a mechanical-type pulse, such as a piezoelectric or magnetostrictive one, when the method and the apparatus according to the invention are applied to a high-resolution gas chromatographic system with capillary column, it is possible to have two cases of a reciprocal disposition of container 10 or 12 and capillary column 66, the first one of these cases being indicated in FIG. 7. According to said figure, the container 10 or 12 shows an outer diameter which is smaller than the inner diameter of the capillary column 66 or of an enlarged end 67 of same, and is therefore inserted into the injector as far as to penetrate with its end section into the inlet opening of the capillary column 66. In this case, the emission of liquid sample under the stated conditions is only conditioned by the fact that the neck 14 does not touch any component and in particular the column 66 wall. Both during sample injection and after this operation, a current of carrier gas is present, which penetrates into the column through the hollow space existing between the column wall and container 10, as indicated by arrows 68.

On the contrary, the case in which the capillary column has an inner diameter smaller or equal to the outer diameter of container 10 or 12 is illustrated, for the two types of container, in FIGS. 8 and 9. In this case, the injector body 70 shows a neck 72, which advantageously has an axial length as small as possible and on the two sides of which there are positioned the column 66 and the container 10 or 12, the latter being preferably housed in a protecting collar 74, which provides for seating of said container 10 or 12 on the inner wall of the injector. In this case, it is advisable, as already said, (i) that the distance between the outlet neck 14 or 16 of container 10 or 12 and the column 66, as measured in an axial direction, be as small as possible, for instance 10 mm maximum, (ii) that the injection pressure of the jet into the neck 14 or 16 be sufficient for maintaining the latter in such a condition as to give rise to a very small opening angle of the jet, and (iii) that the axial alignment of the neck 14 and column 66 be perfect.

It is particularly important in this case that, during injection, the carrier feeding, always according to arrows 68, be discontinued to avoid having the carrier gas drag the outside part of the injected sample, especially if the latter contains easily vaporizable substances.

The system according to the invention, herein described as an example, has proved to be very useful in particular for capillary columns with very small diameters, according to the present trend in this field.

Finally, it should also be noticed that the embodiments of the present invention as above illustrated and described can be submitted to several changes and variations without departing from the spirit and scope of the invention itself, these variations comprising the use of an automatic sampler, wherein the container is automatically filled and wherein sample emission occurs through several jets of sample.

What is claimed is:

1. A method for reproducibly injecting a very small, volumetrically controlled liquid sample for chromatographic analysis, said method comprising the steps of:
   (a) preparing a sample container having a larger volume than the desired sample volume and having a pipette- or nozzle-shaped neck at its outlet, terminating in an opening with a diameter of 1–100 $\mu m$;
   (b) introducing into said container a volume of liquid sample greater than the desired sample volume, in such a manner that a meniscus of the sample liquid forms at said outlet opening, and positioning the filled sample container for sample injection into the chromatographic system; and
   (c) applying to the liquid inside the sample container at least one pressure pulse of controlled duration and amplitude, the maximum amplitude of each said pressure pulse being higher than the pressure necessary to overcome the surface tension of the sample liquid at said meniscus, the duration being sufficient to eject a desired volume of sample liquid, and the pressure drop at the end of each pulse being sufficiently abrupt as to avoid formation of a droplet of sample which is not ejected but instead adheres to said outlet opening.

2. A method according to claim 1, wherein said sample container further comprises a zone of small volume, opposite to the outlet opening and usually not filled with liquid, said zone communicating with a source of gas under regulatable pressure, through a valve whose opening time is controllable, and a duct, said duct having a small volume between the valve and the container; and wherein said pressure pulse is controlled by regulating said gas pressure and controlling the opening time of said valve.

3. A method according to claim 2, wherein said gas pressure is from 1 to 10 atmospheres, and said valve opening time is from 1 millisecond to 1 second.

4. A method according to claim 1, wherein each pressure pulse is produced by magnetostriction or by piezoelectric means.

5. A method according to claim 4, wherein at least part of said sample container, in the portion thereof containing the liquid sample, cooperates with a piezoelectric transducer and wherein said transducer is submitted to at least one electric pulse to give rise to a corresponding pressure pulse in the liquid inside the container.

6. A method according to claim 4, wherein at least part of said container, in the portion thereof containing the liquid sample, is made of nickel; wherein a control device with magnetostrictive actuation cooperates with the nickel part of said container, when the latter is in operative position; and wherein at least one current pulse having an adjustable amplitude is applied using said control device to give rise to a corresponding pressure pulse in the liquid contained in the nickel part of the container.

7. A method according to claim 1, wherein the diameter of the sample container outlet opening is 1–30 μm.

8. A method according to claim 1, wherein the amount of sample injected is 10 picoliters–50 nanoliters.

9. A method according to claim 8, wherein the entire sample is injected directly into a capillary column in a high-resolution gas chromatographic system, without any sample splitting.

10. An apparatus for volumetrically controlled and reproducible injection of small quantities of liquid sample directly into a capillary column of a high-resolution gas chromatographic system without use of a sample splitter, comprising, in combination with an on-column sample injection device for a high-resolution gas chromatographic system:

a sample container having a volume greater than a desired liquid sample volume and having a pipette- or nozzle-shaped neck at its outlet, terminating in an opening with a diameter of 1–100 μm;

positioning means for operatively positioning said sample container in said on-column sample injection device, for injection of a sample through said outlet opening and directly into a capillary column; and pulse means communicating with said container for applying to a liquid inside the container at least one pressure pulse of controlled amplitude and duration, and ending in an abrupt pressure drop.

11. An apparatus according to claim 10, further comprising a source of gas under pressure and means for regulating its pressure; connecting means for pneumatically connecting said gas source to the sample container on the side thereof opposite to the outlet opening, said connecting means comprising a valve, means to control its opening time, and at least one duct connecting said valve to the sample container, said duct being sized in such a way as to minimize the gaseous volume between liquid in the sample container and the control valve.

12. An apparatus according to claim 11, wherein said pressure regulating means is capable of adjusting the gas pressure to a value between 1 and 10 atmospheres and said valve control means is capable of controlling the opening time of the valve to a time interval between 1 millisecond and 1 second.

13. An apparatus according to claim 10, wherein said pulse means comprises at least one transducer capable of producing at least one pressure pulse of high amplitude and short duration in the sample container; a pulse source for exciting said transducers; and means for adjusting at least one of the amplitude or the number of the pulses.

14. An apparatus according to claim 13, wherein said transducer is a piezoelectric tranducer, and said pulse source is a source of electric pulses of high amplitude and steep drop-off.

15. An apparatus according to claim 14, wherein said sample container is made of glass or fused silica and is surrounded, near to the outlet opening thereof, by a piezoelectric transducer embedded in a small block of a plastic material.

16. An apparatus according to claim 13, wherein the sample container has at least a part thereof made of nickel in the portion containing the liquid sample; wherein the transducer comprises a magnetostrictive device capable of acting on said container part when in its operative position within a seat provided in said magnetostrictive device, and actuating means for applying to said magnetostrictive device at least one current pulse having an adjustable amplitude, thereby producing a corresponding pressure pulse acting on the liquid contained in the nickel part of said container.

17. An apparatus according to claim 16, wherein said pulse has a duration which depends on the frequency of mechanical resonance of the magnetostrictive device and is adjustable in amplitude.

18. An apparatus according to claim 10, further in combination with a capillary column; wherein said sample container has at least an end section having a maximum size smaller than the inner diameter of said capillary column where chromatographic separation occurs; and wherein said positioning means cooperates with said on-column injection device for axially controlling the sample container position so that its end section penetrates into the column inlet opening without touching the walls thereof.

19. An apparatus according to claim 10, further in combination with a capillary column; wherein said capillary column has an inner diameter smaller than the neck of said sample container; and wherein said positioning means cooperates with said injection device for reciprocally aligning and axially centering the chromatographic column inlet end and the sample container outlet end in an axially spaced position at a distance not exceeding 10 mm.

20. An apparatus according to claim 19, wherein said chromatographic system further comprises means to discontinue carrier gas feeding during injection.

21. An apparatus according to claim 19 which further comprises a protecting collar for seating the sample container outlet end on the inner wall of the injector.

22. An apparatus according to claim 10, wherein the diameter of the sample container outlet opening is 1–30 μm.

* * * * *